United States Patent
Banov

(10) Patent No.: US 9,763,934 B2
(45) Date of Patent: Sep. 19, 2017

(54) SYNERGISTIC EFFECT OF POLOXAMER-BASED COMPOSITION AND ITRACONAZOLE ON FUNGUS AND YEAST

(71) Applicant: Professional Compounding Centers of America (PCCA), Houston, TX (US)

(72) Inventor: Daniel Banov, Sugar Land, TX (US)

(73) Assignee: Professional Compounding Centers of America, Houston, TX (US)

(*) Notice: Subject to any disclaimer, the term of this patent is extended or adjusted under 35 U.S.C. 154(b) by 328 days.

(21) Appl. No.: 14/307,138

(22) Filed: Jun. 17, 2014

(65) Prior Publication Data

US 2015/0250727 A1 Sep. 10, 2015

Related U.S. Application Data

(60) Provisional application No. 61/948,173, filed on Mar. 5, 2014.

(51) Int. Cl.
| | |
|---|---|
| *A61K 9/14* | (2006.01) |
| *A61K 31/496* | (2006.01) |
| *A61K 9/00* | (2006.01) |
| *A61K 31/137* | (2006.01) |
| *A61K 31/4174* | (2006.01) |
| *A61K 31/4196* | (2006.01) |
| *A61K 31/506* | (2006.01) |
| *A61K 31/513* | (2006.01) |
| *A61K 31/5375* | (2006.01) |

(52) U.S. Cl.
CPC .......... *A61K 31/496* (2013.01); *A61K 9/0073* (2013.01); *A61K 9/146* (2013.01); *A61K 31/137* (2013.01); *A61K 31/4174* (2013.01); *A61K 31/4196* (2013.01); *A61K 31/506* (2013.01); *A61K 31/513* (2013.01); *A61K 31/5375* (2013.01)

(58) Field of Classification Search
CPC . A61K 9/12; A61K 9/14; A61K 9/141; A61K 9/143; A61K 9/146; A61K 9/48; A61K 9/4841

USPC .................................................. 424/464–490
See application file for complete search history.

(56) References Cited

U.S. PATENT DOCUMENTS

| | | | |
|---|---|---|---|
| 2006/0078618 A1* | 4/2006 | Constantinides | A61K 9/0019 424/489 |
| 2008/0160067 A1* | 7/2008 | Boeckh | A61K 9/0019 424/441 |
| 2009/0214656 A1* | 8/2009 | Berndl | A61K 9/146 424/489 |

OTHER PUBLICATIONS

Quadir (Characterization of Newly Developed Micronized Poloxamer for Poorly Soluble Drugs; Control Release Society meeting, Jun. 2005).*

* cited by examiner

*Primary Examiner* — Micah-Paul Young
(74) *Attorney, Agent, or Firm* — David G. Woodral; Scott R. Zingerman; Gable Gotwals

(57) ABSTRACT

A pharmaceutical composition for the treatment of yeast and fungal infections is provided. The composition may include a micronized poloxamer composition as excipient and itraconazole as active pharmaceutical ingredient (API). The micronized poloxamer composition may include a combination of poloxamer 188 and poloxamer 407. Additionally, micronized poloxamer-based composition, used as a surfactant, may help to break out or disrupt the membrane of microorganisms' cells within biofilm, thus allowing APIs, such as itraconazole, to improve their action and effectiveness against fungus and yeast infections. Additionally, poloxamer-based composition may be delivered to the infected site by different administration routes, such as orally, topically, via nasal, lung inhalation, and transdermal delivery. Due to the synergistic effect of poloxamer-based composition, itraconazole may have improved solubility, and dispersibility, thus decreasing side effects and time of treatment.

18 Claims, 3 Drawing Sheets

SYNERGISTIC EFFECT OF POLOXAMER-BASED COMPOSITION AND ITRACONAZOLE ON FUNGUS AND YEAST

CROSS-REFERENCE TO RELATED APPLICATIONS

This application is a continuation-in-part of U.S. Patent Application 61/948,173, filed Mar. 5, 2014, entitled Poloxamer-based Pharmaceutical Composition for Treating Fungal and Yeast Infections and Methods Thereof, the entirety of which is incorporated herein by reference as if set forth herein.

BACKGROUND

Field of the Disclosure

The present disclosure relates in general to therapeutic formulations, and more particularly, to a poloxamer-based composition having itraconazole. This composition may be employed in the treatment of fungal and yeast infections.

Background Information

Fungi may cause a wide variety of diseases in humans. While some fungi may cause infections limited to the outermost layers of the skin and hair (superficial mycoses), other fungi may cause cutaneous mycoses by penetrating the keratinized layers of the skin, hair, and nails, and triggering pathologic changes in the host. Subcutaneous mycoses may cause infections in the dermis, subcutaneous tissues, muscle and fascia and are often chronic. Systemic mycoses may originate primarily in the lung and may cause secondary infections in other organ systems in the body.

Conventional treatments for fungal and yeast infections may include topical and oral drugs. Orally administered drugs may be generally more effective than topically applied ones, besides the oral route may generally be the most convenient and carries the lowest cost, however, some drugs may cause gastrointestinal irritation, and then there is a need for rapid delivery of drug than intended. Otherwise, by delivering drugs almost directly to the site of action, the risk of systemic side effects may be reduced; however, skin irritation may result in some topical ingredients.

Generally, the conventional treatment for fungal and yeast infections may include antifungals as active pharmaceutical ingredients (APIs). Topical and oral antifungal used in different kinds of human organs may be effective for treating fungal and yeast infections in human, but most antifungal drugs may cause different kinds of side effects. However, these side effects may be reduced by the use of specific base compositions that may act in a synergistic effect with APIs and improving the dispersibility of APIs. Additionally, despite progress in the medical field, there are still difficulties (slow healing, not efficient dispersibility of APIs) on the fungus treatment for nasal and lung fungal infections, these difficulties mainly affect people living in certain geographic areas, and those with immune deficiency.

For the aforementioned reasons, there is a need for an improved treatment for yeast and fungal infections which may include excipients that may allow the production of an effective composition, thus providing more residence time and exhibiting less side effects.

The following reference is related to the background of the present invention: National Committee for Clinical Laboratory Standards (1997). Reference method for broth dilution antifungal susceptibility testing of yeasts: approved standard. NCCLS document M27-A. National Committee for Clinical Laboratory Standards, Wayne, Pa.

The following reference is related to the background of the present invention: Promega (2013). CellTiter 96® Non-Radioactive Cell Proliferation Assay Technical Bulletin. Available at: http://www.pronnega.conn/resources/protocols/technical-bulletins/0/celltiter-96-non-radioactive-cell-proliferation-assay-protocol (Accessed: 15 May 2014).

The following reference is related to the background of the present invention: Ramage G., Walle K. V., Wickes B. L. López-Ribot J. L. (2001). Standardized Method for In Vitro Antifungal Susceptibility Testing of *Candida albicans* Biofilms. Antimicrobial Agents and Chemotherapy 45(9): 2475-2479.

SUMMARY

The present disclosure may include a therapeutic formulation for the treatment of yeast and fungal infections. The formulation may treat not only mucosal tissues, but also skin; and may be administered orally, topically, via nasal, lung inhalation, and transdermal delivery. The disclosed poloxamer-based composition may include at least one agent as active pharmaceutical ingredient (API) and a combination of two or more micronized poloxamers as excipients. According to an embodiment, a suitable API may be itraconazole, while suitable micronized poloxamers may include poloxamer 188 and poloxamer 407. Poloxamer-based composition may include poloxamer 188 in concentrations of about 0.1% by weight to about 5% by weight, with about 1% by weight being preferred; and poloxamer 407 in concentrations of about 0.1% by weight to about 5% by weight, with about 1% by weight being preferred.

According to an embodiment, present micronized poloxamer-based composition may be in combination with at least one antifungal agent. In further embodiments, disclosed micronized poloxamer composition may be in combination with at least one antibiotic. Micronized poloxamer composition in combination with any suitable APIs may work together in a synergistic effect. According to one embodiment, poloxamer based composition may be in combination with itraconazole. Additionally, micronized poloxamer-based composition, used as a surfactant, may help to break out or disrupt the membrane of microorganisms' cells within biofilm, thus allowing APIs, such as itraconazole, to improve their action and effectiveness against fungus and yeast infections.

Micronized poloxamer composition may be in sterile granules or powdered form that may be combined with any suitable sterile aqueous solutions or liquid carrier, such as water, saline solution or sodium chloride solution with or without a stabilizing agent. In one embodiment, micronized poloxamer composition may be packed in capsules. According to one embodiment, micronized poloxamer composition may have small particle size between about 30 μm to about 70 μm, most suitable of about 50 μm, and in combination with any suitable APIs, micronized poloxamer composition may be used for treating fungal and yeast infections.

Itraconazole concentrations may depend upon the administration route, according to an embodiment, poloxamer-based composition may include itraconazole in concentrations from about 5 mg/vial to about 100 mg/vial, with about 40 mg/vial to about 50 mg/vial being preferred. The synergistic effect of poloxamer-based composition may provide improved dispersibility of the itraconazole, thus decreasing treatment time and side effects occurrence.

According to one embodiment, micronized poloxamer composition may increase the solubility, dispersibility and action of other components, such as APIs, within poloxamer-based composition.

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
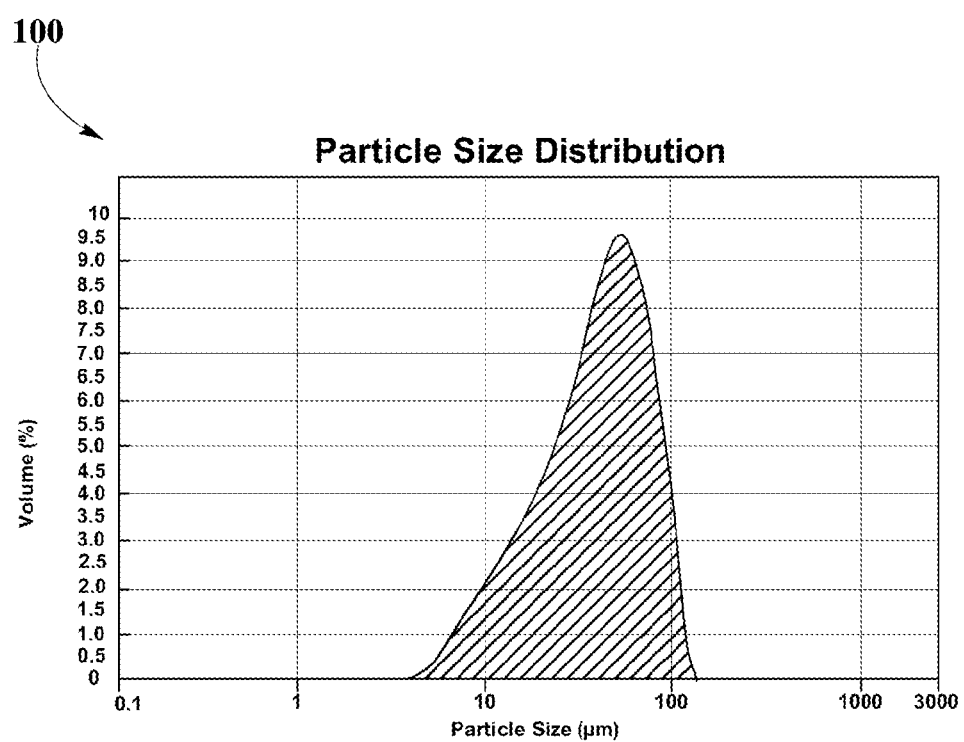
FIG. 1 is a logarithmic graph illustrating the results of particle size test and depicting particle size distribution of micronized poloxamers, according to an embodiment.

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms may have the following definitions:

"Active Pharmaceutical Ingredient (API)" refers to a chemical compound which induces a desired pharmacological, physiological or synergistic effect (when combined with other compositions) and may include agents that are therapeutically, prophylactically, or cosmeceutically effective.

"Excipient" refers to a substance added to a therapeutic formulation in order to provide suitable consistency or form the formulation.

"Infection" refers to the invasion and multiplication of microorganisms in a body tissue, especially that causing local cellular injury due to competitive metabolism, toxins, intracellular replication, or antigen-antibody response.

"Microprilling" refers to a process where solid spherical microprills may be produced from liquid, tablets or encapsulated ingredients having a diameter of a few microns.

"Minimum Inhibitory Concentration (MIC)" may refer to the lowest concentration of an antimicrobial that may inhibit the visible growth of a microorganism after overnight incubation.

"Mucosal membrane" refers to a moist membrane that may line passageways and structures in the body that lead to the outside environment.

"Poloxamer" refers to a non-ionic triblock copolymer having surfactant properties. Poloxamers may be used as thickening agents, gel formers, co-emulsifiers, solubilizers, and consistency enhancers in creams and liquid emulsions.

"Treating" and "Treatment" refers to a reduction in severity and/or frequency of symptoms, elimination of symptoms and/or underlying cause, prevention of the occurrence of symptoms and/or their underlying cause, and improvement or remediation of damage.

DESCRIPTION OF THE DRAWINGS

The present disclosure may relate to a composition of ingredients that, in one embodiment may be a composition for treating yeast and fungal infections. The composition may include a combination of two or more micronized poloxamers as excipients, and itraconazole as a suitable active pharmaceutical ingredient (API). According to an embodiment, disclosed composition may be administered orally, topically, via nasal, lung inhalation and transdermal delivery.

Poloxamer Particle Size and Distribution

FIG. 1 is a logarithmic graph 100 illustrating the results of particle size test and depicting particle size distribution of microprilled poloxamers. Logarithmic graph 100 may demonstrate volume percentage on the "y" axis, and particle size in microns on the "x" axis. Microprilled poloxamers were employed only in direct compression, where microprilled poloxamers may exhibit favorable blend homogeneity. Additionally, segregation problem may be eliminated during direct compression. According to an embodiment, microprilled poloxamers may have an average size of 50 µm; a small percentage of micronized poloxamers may have a particle size between about 10 µm to about 20 µm, while the majority of micronized poloxamers may have a particle size of about 50 µm.

Micronized Poloxamer Composition

Figure 2:
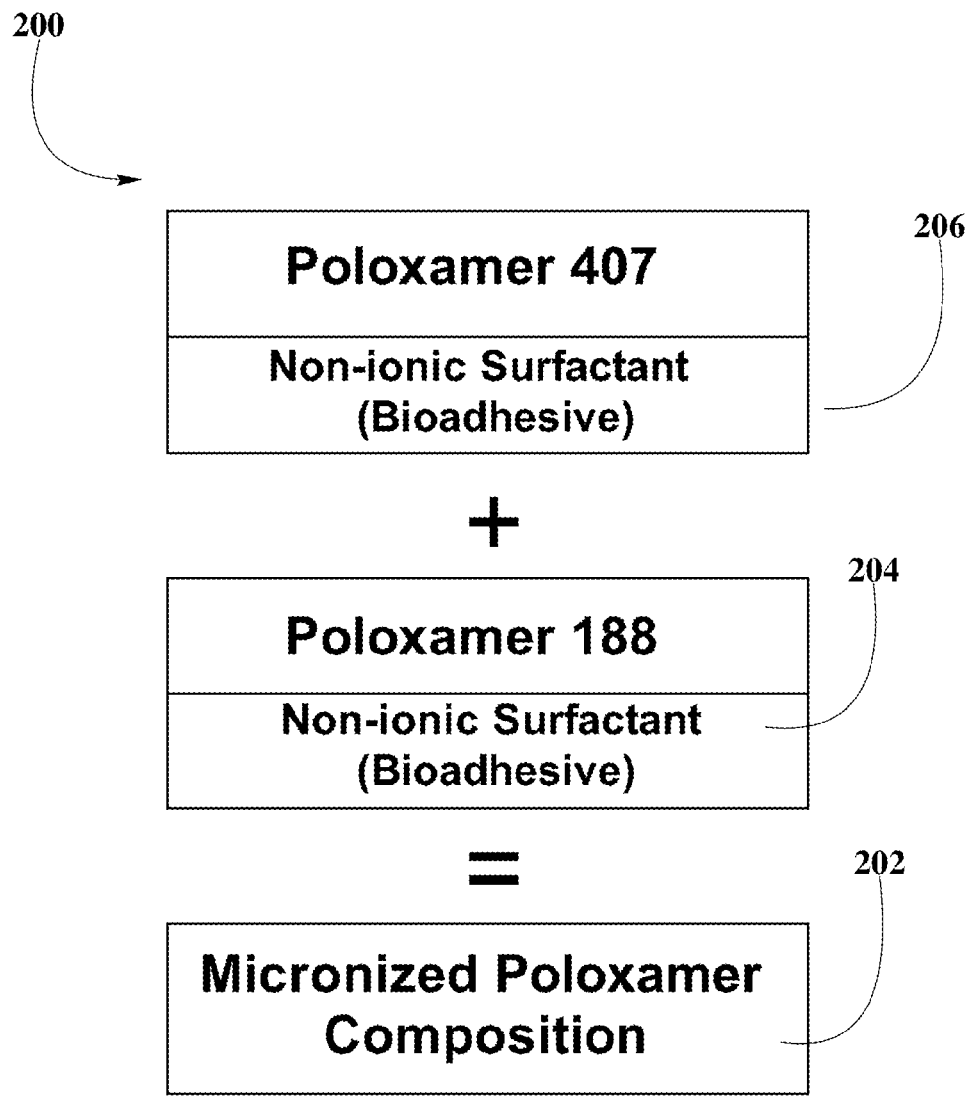
FIG. 2 is a block diagram of micronized poloxamer composition, according to an embodiment.

FIG. 2 is micronized poloxamer composition block diagram 200, according to an embodiment. The present disclosure may refer to a poloxamer-based composition used for treating fungal and yeast infections. The poloxamer-based composition may include a micronized poloxamer composition 202 as excipient. According to some embodiments, micronized poloxamer composition 202 may include poloxamer 188 204 and poloxamer 407 206, which may be employed for treating fungal and yeast infections. Poloxamer 188 204 may be included in concentrations of about 0.1% by weight to about 5% by weight, with about 1% by weight being preferred; and poloxamer 407 206 in concentrations of about 0.1% by weight to about 5% by weight, with about 1% by weight being preferred.

Micronized poloxamer composition 202 may be manufactured in an apparatus where a low-frequency acoustic field is applied, in order to facilitate the mixing process. Suitable concentrations of poloxamer 188 204 and poloxamer 407 206 may be deposited in a vessel which may be subjected to a low-frequency acoustic field in the axial direction, thus resulting in second order bulk motion of the fluid, known as particle collisions. Particles in the container are excited by collisions with the vessel base and collisions with other particles in the container that may result in harmonic vibrations of the vessel with poloxamer 188 204 and poloxamer 407 206. The particle motions are dependent upon the vibration amplitude, frequency, and the resultant accelerations that the particles undergo. The chaotic motions created within the mixing vessel may cause a great degree of particle-to-particle disorder, microcell mixing, as well as creating bulk mixing flow in the solid-solid systems. In order to manufacture micronized poloxamer composition 202, poloxamer 188 204 and poloxamer 407 206 may be mixed with a mixing length of about 50 µm, at a mechanical resonance of about 60 Hz.

Particle size of micronized poloxamer composition 202 may range between about 30 μm to about 70 μm, where about 50 μm may be preferred. The advantages of micro-prilling in micronized poloxamer composition 202 may include stronger solubilization properties, controlled dissolution rate, reduction of die-wall friction, achievement of homogeneous blend, elimination of dose dumping and effectiveness as water soluble lubricant.

Furthermore, poloxamer based composition may have solubility properties dictated by the hydrophobic portion of the micronized poloxamers. The use of micronized poloxamers may increase the solubility and dispersibility of the active pharmaceutical ingredient that is employed, thus the drug may have enhanced treatment properties. Furthermore, the properties of each poloxamer may vary in terms of molecular weight, appearance, hydrophilicity/hydrophobicity, and solubility, which may be determined by the chain length of the polyxyethylene (EO-) units and polyoxypropyene (PO-) units.

Itraconazole

Itraconazole is a triazole antifungal which may slow the growth of fungi that causes infection. Itraconazole is widely used to treat fungal infections in the lungs, fingernails, and toenails, as well as yeast infections in the throat or esophagus.

The mechanism of action of itraconazole may inhibit the fungal-mediated synthesis of ergosterol. Itraconazole is pharmacologically distinct from other azole antifungal agents in that it may be able to inhibit both the hedgehog signaling pathway and angiogenesis. These distinct activities may be unrelated to inhibition of the cytochrome P450 lanosterol 14 alpha-demethylase as the exact molecular targets responsible remain unidentified. Functionally, the antiangiogenic activity of itraconazole may be linked to the inhibition of glycosylation, VEGFR2 phosphorylation, trafficking, and cholesterol biosynthesis pathways. Evidence may suggest that the structural determinants for inhibition of hedgehog signaling by itraconazole may be recognizably different from those associated with antiangiogenic activity.

Poloxamer Based Composition having Itraconazole

In order to produce poloxamer based composition having itraconazole, suitable concentrations of itraconazole may be added to micronized poloxamer composition 202. Suitable concentrations of itraconazole may be included in concentrations from about 5 mg/vial to about 100 mg/vial, with about 40 mg/vial to about 50 mg/vial being preferred.

Poloxamer based composition having itraconazole may improve the inhibition of the fungal cell wall synthesis, may disrupt the cell membrane of the microorganism, may affect the ribosomal subunits to inhibit protein synthesis, and may alter protein synthesis, thus leading to fungal cell death.

According to an embodiment, poloxamer based composition having itraconazole may be efficient and effective in treating fungal and yeast infections. The composition may treat infections caused by microorganisms, such as *Aspergillus niger, Aspergillus fumigatus, Blastomyces dermatitidis, Sporothrix schenckii, Histoplasma capsulatum, Trichophyton rubrum, Rhizopus oryzae, Candida albicans, Cryptococcus neoformans*, and *Cryptococcus gattii*, among others.

Moreover, the minimal inhibitory concentration (MIC) of micronized poloxamer composition having itraconazole was tested against microorganisms, such as *Aspergillus niger, Aspergillus fumigatus, Candida albicans*, and *Rhizopus oryzae*. The results showed the MIC values against filamentous fungi and yeast strains ranging from about 0.025 ug/mL to about 0.2 ug/mL. The low MIC value may demonstrate that poloxamer-based composition may enhance the properties of itraconazole.

Poloxamer-based composition may allow itraconazole to be driven directly into the site of treatment, thus increasing the solubility and dispersibility of itraconazole and decreasing treatment time. Furthermore, the synergistic effect of micronized poloxamer composition 202 may improve the dispersibility of itraconazole, thus enhancing the action of the poloxamer-based composition.

Poloxamer-based composition, used as a surfactant, may help to break out or disrupt the membrane of microorganisms' cells within biofilm, thus allowing APIs, such as itraconazole, to improve their action and effectiveness against fungus and yeast infections.

According to another embodiment, micronized poloxamer composition 202 may be used in combination with any suitable APIs for treating bacterial infections.

Antifungal Agents

According to some embodiments, antifungal agents may include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, bifonazole, butoconazole, fenticonazole, isoconazole, omoconazole, sertaconazole, albaconazole, isavuconazole, abafungin, amorolfin, butenafine, and combinations thereof.

Antibiotic Agents

According to some embodiments, antibiotic agents may include aminoglycosides, amikacin, gentamicin, kanamycin, neomycin, netilmicin, tobramycin, paromomycin, spectinomycin, ansamycins, geldanamycin, herbimycin, rifaximin, carbacephem, loracarbef, carbapenems, ertapenem, doripenem, meropenem, cephalosporins, cefadroxil, cefazolin, cefalotin, cefalexin, cephalosporins, cefaclor, cefamandole, cefoxitin, cefprozil, cefuroxime, cephalosporins, cefixinme, cefdinir, cefditoren, cefoperazone, cefotaxime, cefpodoxime, ceftazidime, ceftibuten, ceftizoxime, ceftriaxone, cephalosporins, cefepime, cephalosporins, ceftaroline fosamil, ceftobiprole, glycopeptides, teicoplanin, vancomycin, telavancin, lincosamides, clindamycin, lincomycin, lipopeptide, daptomycin, macrolides, azithromycin, clarithromycin, dirithromycin, erythromycin, roxithromycin, troleandomycin, telithromycin, spiramycin, monobactams, aztreonam, nitrofurans, furazolidone, nitrofurantoin, oxazolidononens, linezolid, posizolid, radezolid, torezolid, penicillins, amoxicillin, ampicillin, azlocillin, carbenicillin, cloxacillin, dicloxacillin, flucloxacillin, mezlocillin, methicillin, nafcillin, oxacillin, penicillin, piperacillin, temocillin, ticarcillin, polypeptides, bacitracin, colistin, polymyxin b, quinolones, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, sulfonamides, mafenide, sulfadiazine, sulfamethizole, sulfamethoxazole, sulfanilimide (archaic), sulfasalazine, sulfisoxazole, tetracyclines, demeclocycline, doxycycline, minocycline, oxytetracycline, tetracycline, clofazimine, dapsone, capreomycin, cycloserine, ethambutol, ethionamide, isoniazid, pyrazinamide, rifabutin, rifapentine, streptomycin, arsphenamine, chloramphenicol, fosfomycin, metronidazole, mupirocin, quinupristin/dalfopristin, thiamphenicol, tigecycline, trimethoprim, and combinations thereof.

Administration Routes

Figures 3, 3A, 3B:
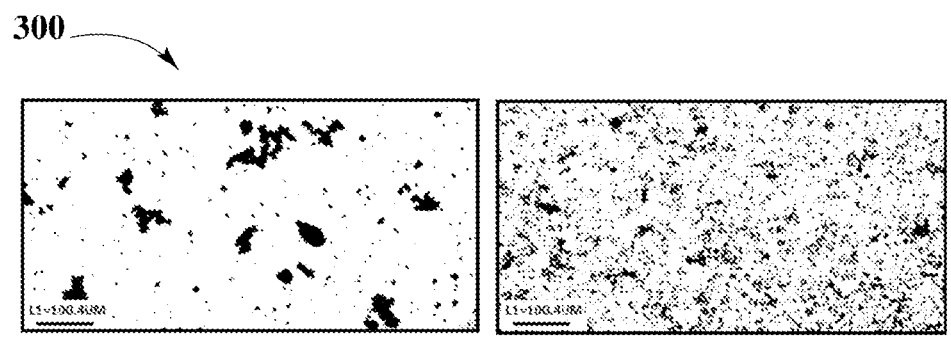
FIG. 3 depicts a comparison between the particle size of itraconazole when dispersed in purified water and the particle size of itraconazole in combination with micronized poloxamer composition when dispersed in purified water, according to an embodiment.

According to an embodiment, poloxamer-based composition having itraconazole may be delivered employing suitable inhalation devices, such as aerosols, inhalers, and nebulizers, among others. For this administration route, poloxamer-based composition having itraconazole may be obtained in micronized powder. The micronized powder may be employed to fill capsules, which may be used for the administration of the composition. In other embodiments, poloxamer-based composition having itraconazole, in powder form, may be dissolved in suitable solvents in order to obtain the composition in solution form. Suitable solvents may include sterile solution of sodium chloride, and water, among others.

In some embodiments, poloxamer-based composition having itraconazole may be delivered through a mucous membrane, such as nasal cavity. In further embodiments, poloxamer-based composition may also be applied on skin. For this administration route, poloxamer-based composition having itraconazole may be produced as a bioadhesive gel, which may be applied directly to the mucosal membranes for the extended and controlled release of itraconazole. Furthermore, poloxamer-based composition in combination with any suitable APIs, such as itraconazole, may be administered orally, topically, and via transdermal delivery.

Testing Antimicrobial Activity of Itraconazole and Micronized Poloxamer Composition Materials: Itraconazole EP Micronized (lot number C149307) and PCCA Formula #10342 (4 g of Itraconazole EP Micronized +37.574 g of Poloxamer composition) were provided by PCCA (Houston, Tex., USA) as powders. Itraconazole and PCCA Formula #10342 were prepared on the day of the assay. Fluconazole and amphotericin B were obtained as powders and stored at 4° C. Stock solutions (10.24 mg/mL) of these two reference actives were prepared in sterile water.

Strain: *Candida albicans* isolate ATCC 90028 was obtained from American Type Culture Collection (Manassas, Va.), and used in the course of this study.

Methods: To determine antimicrobial activity of itraconazole and micronized poloxamer composition 202 against biofilms of *Candida albicans*, an antifungal biofilm susceptibility testing was developed in conditions where a Minimum Biofilm Inhibitory Concentration (MBIC) of itraconazole in a micronized poloxamer composition 202, micronized poloxamer excipient, itraconazole, fluconazole and amphotericin B was measured for the *C. albicans* biofilm according to the NCCLS M27-A broth microdilution method (NCCLS, 1997). The testing medium used for growing was RPMI 1640 (American Biorganics, Inc., Niagara Falls, N.Y.) supplemented with L-glutamine (Sigma Aldrich®). Yeast inocula (100 μL of $1\times10^6$ cells/mL) were added to each well of 96-well microtiter plates (Corning) and incubated at 37° C. for 48 h. After biofilm formation, medium was aspirated and non-adherent cells were sterile phosphate-buffered saline (PBS, Sigma Aldrich®). The antifungal drug and poloxamer mixture solutions (samples) were then added to the biofilms in serially diluted concentrations (1,024 to 0.5 μg/mL, from stock [concentrated] solutions of each sample prepared in RPMI medium directly) and incubated for a further 48 h at 35° C. A series of sample-free wells and biofilm-free wells were also included to serve as positive and negative controls, respectively. The MBIC was defined as the lowest concentration of sample that produced a 50% reduction of fungal growth compared with the growth control. Cell viability was determined by using CellTiter 96® Non-Radioactive Cell Proliferation Assay (Promega, 2013).

Results and Discussion: All biofilms formed on the microtiter plates over 48 h displayed consistent CellTiter 96® dye solution readings when the intensity of the colorimetric product was measured in a microtiter plate reader at 570 nm. The MBIC value of itraconazole in a micronized poloxamer composition 202 (expressed as concentration of itraconazole) showed efficient result in comparison with the MBIC values for raw itraconazole, fluconazole and amphotericin B tested against *C. albicans* ATCC 90028, as reported in Table 1. Micronized poloxamer composition 202 improved the antimicrobial potential of itraconazole approximately 10-fold. Biofilm from *C. albicans* strain tested was intrinsically resistant to fluconazole (MBIC>1024 μg/mL). The polyene antifungal amphotericin B was highly active (MBIC=0.5 μg/mL) against *C. albicans* ATCC 90028. The findings for fluconazole and amphotericin B are in accordance with the literature (Ramage et al., 2001).

As may be seen, itraconazole may have an increased in vitro antimicrobial activity against *Candida* biofilms when associated with the micronized poloxamer composition 202 excipient. It may be due to the benefits caused by the base in terms of the dissolution rate and saturation solubility of the poorly water-soluble itraconazole, providing a higher in vitro dissolved drug concentration that induced an enhanced inhibition of microbial growth (considering the MIC). Micronized poloxamer composition 202 with itraconazole may exhibit improved particle size distribution in water and also improved antifungal activity compared to itraconazole alone.

TABLE 1

Minimum Biofilm Inhibitory Concentrations against *C. albicans* ATCC 90028.

| Sample | Minimum Biofilm Inhibitory Concentration (ug/mL) |
|---|---|
| Amphotericin B | 0.5 |
| Fluconazole | >1,024 |
| Itraconazole | 1024 |
| Micronized Poloxamer Composition | >10,240 |
| Itraconazole/Micronized Poloxamer Composition | 98.5 |

The following examples are intended to illustrate the scope of the disclosure. It is to be understood that other procedures known to those skilled in the art may alternatively be used.

EXAMPLES

Example #1

The improvement of the dispersibility of an API when used in combination with micronized poloxamer composition 202 was tested. For this study, itraconazole was chosen as API due to its low solubility in water. FIG. 3A and FIG. 3B depict a comparison 300 between the particle size of itraconazole when dispersed in purified water and the particle size of itraconazole in combination with micronized poloxamer composition 202 when dispersed in purified water. FIG. 3A represents the particle size of itraconazole alone at about 1%, and FIG. 3B illustrates the particle size of poloxamer based composition having itraconazole at about 1%. Both at 200× magnification.

As may be seen in FIG. 3A and FIG. 3B, micronized poloxamer composition 202 may optimize the particle size distribution of itraconazole in a solution, thus reducing itraconazole's particle size. Therefore, the synergistic effect of micronized poloxamer composition 202 may be proven by the increased solubility and dispersability of any suitable APIs, such as itraconazole.

Example #2

Micronized poloxamer composition may include poloxamer 407 206 and poloxamer 188 204. Specifically, poloxamer 407 206 may be included in amounts of about 5% by weight to about 25% by weight, most suitable of about 10% by weight; poloxamer 188 204 may be included in amounts of about 5% by weight to about 25% by weight, most suitable of about 10% by weight.

While various aspects and embodiments have been disclosed here, other aspects and embodiments may be contemplated. The various aspects and embodiments disclosed here are for purposes of illustration and are not intended to be limiting, with the true scope and spirit being indicated by the following claims.

What is claimed is:

1. An antifungal composition, comprising:
    about 1% by weight of at least two micronized poloxamers; and
    at least one antifungal composition.

2. The composition of claim 1, wherein the at least two micronized poloxamers are selected from the group consisting of poloxamer 407, poloxamer 188, and combinations thereof.

3. The composition of claim 1, wherein the at least two micronized poloxamers have an average particle size between about 30 μm to about 70 μm.

4. The composition of claim 1, wherein the at least two micronized poloxamers have an average particle size of about 50 μm.

5. The composition of claim 1, wherein the at least two micronized poloxamers and the at least one antifungal composition are contained in a capsule.

6. The composition of claim 1, wherein the at least two micronized poloxamers and the at least one antifungal composition are contained in a capsule.

7. The composition of claim 1, wherein the at least one antifungal composition is administered to treat a fungal or yeast infection of a person.

8. The composition of claim 1, wherein the at least one antifungal composition is administered to at least a portion of the nasal cavity or lungs of a person.

9. The composition of claim 1, wherein the composition is administered in effective dosages of about 2 mL to about 15 mL once or twice a day after reconstitution (solubization) with saline or water.

10. The composition of claim 1, wherein the antifungal composition is selected from the group consisting of amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, bifonazole, butoconazole, fenticonazole, isoconazole, omoconazole, sertaconazole, albaconazole, isavuconazole, abafungin, amorolfin, butenafine, and combinations thereof.

11. A method of providing an antifungal treatment, comprising:
    administering to a patient a composition comprising
        at least two micronized poloxamers; and
        at least one antifungal composition;
    wherein the at least two micronized poloxamers improve effectiveness of the at least one antifungal composition; and
    wherein the at least two micronized poloxamers and the at least one antifungal composition are in solution with the at least two micronized poloxamers being present in solution at about 1% by weight.

12. The method of claim 11, wherein the at least two micronized poloxamers are selected from the group consisting of poloxamer 407, poloxamer 188, and combinations thereof.

13. The method of claim 11, wherein the at least two micronized poloxamers have an average particle size between about 30 μm to about 70 μm.

14. The method of claim 11, wherein the at least two micronized poloxamers have an average particle size of about 50 μm.

15. The method of claim 11, wherein the at least one antifungal composition is administered to treat a fungal or yeast infection of a person.

16. The method of claim 11, wherein the at least one antifungal composition is administered to at least a portion of the nasal cavity or lungs of a person.

17. The method of claim 11, wherein the composition is administered in effective dosages of about 2 mL to about 15 mL once or twice a day after reconstitution (solubization) with saline or water.

18. The method of claim 11, wherein the antifungal composition is selected from the group consisting of amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, bifonazole, butoconazole, fenticonazole, isoconazole, omoconazole, sertaconazole, albaconazole, isavuconazole, abafungin, amorolfin, butenafine, and combinations thereof.

* * * * *